(12) United States Patent
Zhang et al.

(10) Patent No.: US 10,052,201 B2
(45) Date of Patent: Aug. 21, 2018

(54) VALVED STENT FOR MITRAL AND TRICUSPID HEART VALVE REPLACEMENT

(71) Applicant: Peijia Medical Co., Ltd., Suzhou, Jiangsu Province (CN)

(72) Inventors: Yi Zhang, San Diego, CA (US); Ping Ye Zhang, San Diego, CA (US)

(73) Assignee: Peijia Medical Co., Ltd., Suzhou (CN)

( * ) Notice: Subject to any disclaimer, the term of this patent is extended or adjusted under 35 U.S.C. 154(b) by 0 days.

(21) Appl. No.: 15/272,213

(22) Filed: Sep. 21, 2016

(65) Prior Publication Data

US 2018/0078365 A1    Mar. 22, 2018

(51) Int. Cl.
*A61F 2/24*    (2006.01)

(52) U.S. Cl.
CPC .... *A61F 2/2418* (2013.01); *A61F 2220/0016* (2013.01); *A61F 2310/00011* (2013.01)

(58) Field of Classification Search
CPC ......... A61F 2/24; A61F 2/2448; A61F 2/2418
USPC .................................................. 623/2.1–2.19
See application file for complete search history.

(56) References Cited

U.S. PATENT DOCUMENTS

| | | | |
|---|---|---|---|
| 8,236,049 B2 | 8/2012 | Rowe et al. | |
| 8,728,155 B2 | 5/2014 | Montorfano et al. | |
| 8,870,948 B1 | 10/2014 | Erzberger et al. | |
| 8,894,702 B2 | 11/2014 | Quadri et al. | |
| 8,926,691 B2 | 1/2015 | Chau et al. | |
| 9,023,100 B2 | 5/2015 | Quadri et al. | |
| 9,125,740 B2 | 9/2015 | Morriss et al. | |
| 9,241,790 B2 | 1/2016 | Lane et al. | |
| 9,248,014 B2 | 2/2016 | Lane et al. | |
| 9,295,552 B2 | 3/2016 | McLean et al. | |
| 2006/0259135 A1 | 11/2006 | Navia et al. | |
| 2011/0319989 A1 | 12/2011 | Lane et al. | |
| 2012/0179244 A1 | 7/2012 | Schankereli et al. | |
| 2014/0222136 A1 | 8/2014 | Geist et al. | |
| 2015/0173897 A1 | 6/2015 | Raanani et al. | |
| 2015/0209136 A1 | 7/2015 | Braido et al. | |
| 2015/0257881 A1 | 9/2015 | Bortlein et al. | |

(Continued)

FOREIGN PATENT DOCUMENTS

| | | |
|---|---|---|
| EP | 2777616 A1 | 9/2014 |
| EP | 2278944 B1 | 3/2016 |
| WO | 2013104721 A1 | 7/2013 |

OTHER PUBLICATIONS

International Search and Written Opinion of the International Searching Authority for PCT Application No. PCT/US2017/049421 dated Nov. 2, 2017.

(Continued)

*Primary Examiner* — Suzette J Gherbi
(74) *Attorney, Agent, or Firm* — Charles F. Reidelbach, Jr.

(57) ABSTRACT

An implantable valved stent for a patient's heart is formed by a stent supporting a cloth structure. The valved stent includes an upper mounting portion and a lower valved portion. The upper mounting portion has an upper side and a lower side supporting a plurality of hooks extending downwardly from the lower side whereby the implantable valved stent is mounted to the heart when heart tissue is captured between the hooks and the lower side. The lower valved portion extends downwardly from the upper mounting portion and includes a check valve that allows downward flow of the blood and checks upward flow of blood.

19 Claims, 7 Drawing Sheets

(56) References Cited

U.S. PATENT DOCUMENTS

| | | |
|---|---|---|
| 2015/0257882 A1 | 9/2015 | Bortlein et al. |
| 2015/0272737 A1 | 10/2015 | Dale et al. |
| 2015/0328000 A1 | 11/2015 | Ratz et al. |
| 2016/0310268 A1* | 10/2016 | Oba .................. A61F 2/2418 |
| 2017/0128203 A1* | 5/2017 | Zhang ................ A61F 2/2418 |
| 2017/0281337 A1* | 10/2017 | Campbell ........... A61F 2/2409 |
| 2017/0281340 A1* | 10/2017 | Guttenberg ......... A61F 2/2418 |

OTHER PUBLICATIONS

Extended European Search Report of the European Patent Office for EP application 17191047.4 dated Feb. 2, 2018.

\* cited by examiner

VALVED STENT FOR MITRAL AND TRICUSPID HEART VALVE REPLACEMENT

FIELD OF THE INVENTION

The present application relates generally to medical devices and methods, but particularly to a device for replacing native diseased and dysfunctional mitral valves, as well as certain bioprosthetic dysfunctional mitral valves, and encompasses devices and methods for delivering and implanting the same in live beings, animals' or humans' cardiac chambers without the use of external circulatory aid during the normal pumping of the heart. Alternatively it is possible to use the device for the sutureless implantation of mitral valved stents in a temporarily open chamber of the heart while it is still functioning. The device is not limited to systems for delivery of mitral valve devices but may be applicable to other heart valves such as the tricuspid valve.

BACKGROUND

Prostheses in various forms have been used for over five decades to replace dysfunctional heart valves. Each of the four heart valves in the human heart, the aortic, and mitral valves on the left side, or the pulmonary and tricuspid valves on the right side can become dysfunctional in many ways at any time, and an event (infections, structural failures such as tears or disruption of certain components as with the mitral valve chordae, or deformation because of genetic predisposition of valvular material) can disrupt the normal unidirectional flow of blood often with death as a possible outcome. For some situations there is a degree of urgency in addressing a dysfunctional valve. Historically valves have been replaced with the use of "open heart surgery" which is a highly invasive and risky procedure. These procedures can place the very young or old at high risk for procedure-induced mortality. As a result, older patients are often denied open heart surgery and are treated to make the effects more bearable during a descent until death.

The use of less risky and invasive catheter techniques to deliver stents has become widespread. This technique has been used to delivery heart valves in a like manner. Typically the catheter has a distal tip with a capsule that contains the heart valve. The distal tip is threaded through the patient's vascular system to the placement location where it replaces the function of a dysfunctional valve.

There are various ways to arrive at the site of any of the heart valves in an animal or human. The catheter containing the valved stent may be introduced into the heart in antegrade route, meaning following the flow of blood along a vessel or through the heart. Alternatively it may be introduced in retrograde manner, that is, its tip going against the flow of blood through the heart. As an illustrative example, an aortic valved stent is introduced through the femoral artery, the catheter travels retrograde to the flow of blood (against the normal flow of blood in the aorta), traveling the length of the aorta until it reaches the diseased aortic valve and the junction of aorta to the heart where it will be deposited to begin its function.

At present, most of said techniques can be used to provide a variety of options depending on the status and condition of the patient as well as to minimize longitudinal or post intervention complications, and more specifically to eliminate exposure to cardiopulmonary bypass and all its well-known untoward consequences. While the catheter-guided techniques for the aortic and pulmonary valves have been used extensively, now counting over 300,000 patients, these techniques have not yet translated into well-established mitral valve replacement techniques. The reason for this resides in the complexity of the mitral valve, that in effect is a mitral apparatus, consisting of a continuum that begins at the walls of the heart from which papillary muscles emerge that connect to a group of tendon-like filaments termed the chordae tendineae, having the appearance of parachute ropes that reach into the mitral valve leaflets' edges; said leaflets are of different shape and sizes, the anterior mitral leaflet having larger surface that connects to the atrial curtain descending from the aorta, and the posterior mitral leaflet that attaches to the outer or posterior portion of the wall of the heart. Both of these leaflets and chordal mass are contained within a not-so-continuous structure generally termed the annulus. Approach from the atrial side or the ventricular side of the valve to its annular plane poses some difficulties of navigation, not only for the approach, but for the accurate deposition of valved stents coaxially (stent lined with the central axis of the mitral valve), and the capture of the necessary leaflet and annular components to remain in place, seal the periphery between the two chambers and provide the necessary function.

Open surgical replacement has been performed for hundreds of thousands of cases of mitral valve dysfunction, be it stenosis or incompetence until it was realized that often valvular tissue in some disorders was still well preserved in whole or in part. Surgeons devised procedures to repair the malfunction in open heart procedures, a sizable percent of which were durable but only centers of excellence are able to perform the complex surgery. The number of patients affected with the condition of mitral regurgitation or valve incompetence graded in terms of its severity at higher than mild (moderate) and many graded severe is very large reaching many millions worldwide. Oern S., Liddicoat J.: Emerging Opportunities for Cardiac Surgeons within Structural Heart Disease. *J Thorac and Cardiovasc Surgery:* 132: 1258-1261 (2006), describe the incidence of disorders of the cardiac valves in the US population, and show that there are in the order of 2.3 million patients yearly who have dysfunctional mitral valves in various stages of the condition, with approximately 220,000 in the severe category. Of these severe patients only about 23% (48,000) receive the proper treatment for correction of the condition; a large proportion goes untreated and since the report was written over one million patients have died. Present day repair centers can only handle a few.

The translation of surgical repair techniques to catheter guided less invasive techniques began in the late 1990s in the hope of reproducing certain surgical repair techniques. It was met with many disappointments when assessing the reliability of the safety and more particularly the effectiveness of such procedures. The results in many cases are only partially satisfactory with a sizable percentage of incomplete repairs of mitral regurgitation. Although a variety of approaches have been attempted, such as trapping the mitral valve leaflets' central edges and apposing them centrally thus creating a double orifice (reproducing the surgical Alfieri edge-to-edge repair technique with catheters) to reduce mitral regurgitation is the most advanced. Others provide reduction of annular dilatation through the introduction of metallic wires through the coronary sinus vein to circumscribe the mitral valve annulus and reduce its size by constriction, but this also met with disappointing results. A few others purported to correct the condition by repair with minimally invasive procedures but results are poor at best.

In various embodiments, replacement heart valves can comprise certain components that are common to most devices for replacement of heart valves. There is often a component that will act as a support, the frame, usually referred to as the stent. Within this frame or stent, a valvular mechanism is enclosed, often having more flexibility in the case of the so called biological heart valves, as these valvular mechanisms are to undertake the restoration of the valvular function. These valvular mechanisms are comprised of sections of thin material (usually a biological membrane) that are movable under the action of the flow of blood, said sections that can be singular or be in a plurality of two or more sections is often termed the leaflets or valves. Depending on the direction of the flow of blood, these surfaces will move in the same direction, so as to open the orifice that is provided by the stent as large as it is possible without damage to the leaflet when blood flows from one chamber of the heart to the next or towards the outside the heart, and subsequently as the pumping stroke of the heart is finished, blood flow reversal instantaneously occurs and pushes the leaflets in the opposite direction closing the valve and impeding retrograde blood flow or reflux, also called regurgitation. Regurgitation clearly diminished the efficiency of the heart whose function is to maintain flow to all parts of the body.

The valves used for decades as implants for the major part consisted of the same components, namely a stent generally fabricated from polymers reinforced with wire, and a leaflet mechanism. The valved stents of the "new era" of valve therapy, are in general cylindrical tubular frames of metal, cut in such manner and shape that can be compressed to a very small diameter, close to the original diameter of the tube while including the tissue valvular mechanism, such that the whole valve can be threaded through the vasculature with the aid of catheters, in the smaller possible profile to minimize or totally avoid damage to the bioprosthesis and the patients vascular route to the valve in the heart that is to be "replaced". These metal stents are generally made of rust-free very pure stainless steels (alloys of iron and other metals) that require a liquid filled balloon under pressure to expand said stents to their final or nominal diameter, but often in their final expanded diameter are still subject to the pressures the tissue may apply and be deformed inwardly. Other metal alloys used are the so-called shape memory metals that can be compressed to the small diameters desired at specified low temperature ranges and on their own, because of their molecular composition, will expand under the second conditions of temperature (i.e. body temperature) to their original pre-compression nominal diameter, that is, the framework has temperature shape-memory. The stents, in effect the valve, in the "new era" of heart valve therapy are conformed to meet a specified requirement to perform the needed function. This very stringent requirement is the ability to remain in the intended position, or the landing area. That is, it will not dislocate or migrate such that it is in effect anchored for the duration of its use as that patient's valve function is needed. In addition the valved stent must seal the periphery to avoid leakages that can be very damaging to the blood and the health of the patient, and otherwise may require revision or surgery for correction of those events.

The use of stents in aortic valve replacement therapy is mostly for aortic stenosis, a disease that often occurs because of the pathological mineralization of the tissue that constitutes the aortic heart valve. Leaflets of the aortic valve become thickened and calcium deposits by diffusion from the blood plasma within the leaflet tissue and at times on the surface of the tissue, hardening the leaflets and their mobility to the point that they practically close by narrowing (stenosis) the orifice leading from the left ventricle to the aorta so that blood cannot follow a normal flow. The ventricle pumping overexerts its muscle which becomes thickened trying to pump blood through a smaller orifice of the aortic valve and slowly its function decays. The body is deprived of blood and organ conditions and quality of life decreases rapidly. Catheter-guided implanted valved stents that are used to correct the disease rely purely on the force exerted by the stent on the calcified rocky leaflets. These stents are cylindrical in the neighborhood of the valve and the walls of that cylinder exert the pressure to keep the valved stent in the area of the native aortic valve by interference fit. This pressure will be exerted by dilation of the stainless steel valved stent with a balloon, or by the temperature shape memory force of the expanded stent. It is an entirely different set of conditions that are present in the case of mitral valve regurgitation.

Mitral regurgitation (MR) can be caused by many conditions, some are more amenable to the use of valved stents. One form of condition results from changes in the shape and size of the heart, by dilatation of both heart and mitral valve annulus (dilated cardiomyopathy, DCM). This condition alters the valvular function and as such is termed functional mitral regurgitation. It is a vicious cycle, when myocardial (heart muscle) damage results in left ventricle dilation which in turns leads to apical dislodgement of the papillary muscles. These muscles lead to annular dilatation and these two combine to produce mitral regurgitation causing left ventricle overload that results in left ventricle dilatation and the cycle begins again. The annulus and the mitral valve and the atrial curtain has lost its ability to maintain the size of the mitral valve orifice. Dilatation can expand this orifice to almost double its size in extreme cases and leaflets are far apart at a time in the heart cycle (systole) when they should be in apposition and closing the valve orifice to impede reflux into the chamber (atrium) from which fractions of a second previously blood flowed into the ventricle. The annulus is soft and pliable and somewhat less pliable in parts, and exerting pressure radially on it as aortic stents would only lead to more expansion and aggravate the condition.

There are no prosthetic mitral valve devices at present that have been fully developed and commercialized for placement in a dysfunctional mitral valve or replacement of the native mitral valve function by percutaneous means or catheter-guided means. Accordingly, it must be reiterated that there is a very strong need for improved designs of valved stents, and devices of delivery that will result in improved embodiments to replace the function of mitral heart valves, and tricuspid valves for which there are none fully developed at present. Said embodiments must enable the precise delivery, deployment and deposition of valved stents into the atrioventricular annuli and their engagement with minimal complications and restoration of function as near as possible to that of normal healthy human valves. Said embodiments must also prevent the development of peripheric valvular leaks (PVL), that is, the development of leaks between the implanted valved stent and the native valular tissue to which the stent must conform very closely.

SUMMARY

Figure 1:
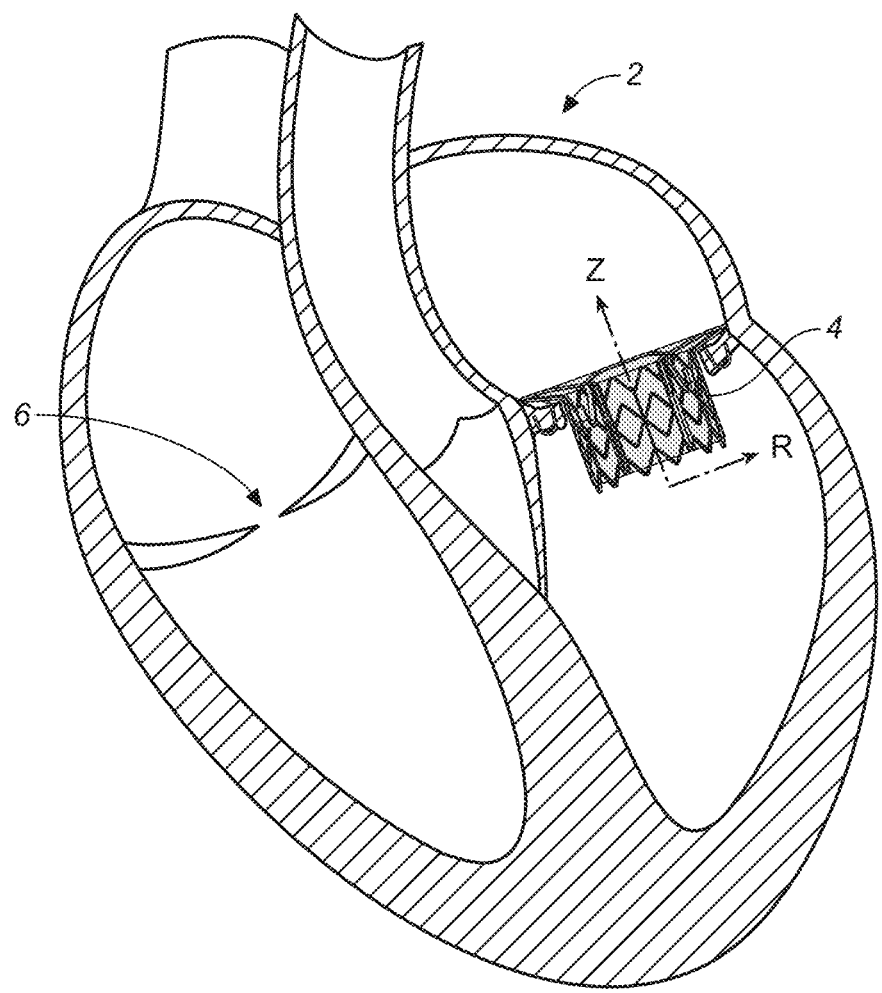
FIG. 1 is a cross sectional view of a human heart with an implanted valved stent.

The invention disclosed herein refers to a device, specifically an artificial heart valve for replacement of a diseased or dysfunctional heart valve in the heart of a patient. The valved stent and the delivery device described below in various embodiments represent improvements intended to facilitate the implantation of a device that will return function to dysfunctional atrioventricular valves and that heretofore are considered extremely difficult to deliver, deploy and function with minimal complications.

The valved stent has two configurations including a transport configuration and an implantation configuration. In the transport configuration the stent is radially collapsed or contracted to facilitate implantation with a tubular device such as a catheter. In the implantation configuration the valved stent is radially expanded proximate to or in the location of implantation. The valved stent can be expanded and customized to varying implantation configurations that depend in part upon a geometry of the implantation location.

In one exemplary use, the valved stent is used to replace a dysfunctional mitral heart valve. In another exemplary use, the valved stent is used to replace a dysfunctional tricuspid valve. In each of these exemplary uses, the valved stent is delivered to the site of the valve using a tubular device such as a catheter.

In the ensuing paragraphs of this summary, three aspects of the valved stent are described. All three aspects of this summary concern the valved stent in its fully or partially expanded state prior to, during, or after installation to replace a diseased valve.

In a first aspect of the disclosure, an implantable valved stent includes a stent supporting a cloth structure that together form the valved stent. The valved stent also includes an upper mounting portion and a lower valved portion. The upper mounting portion includes an upper side and a lower side. The lower side includes a plurality of N hooks extending downwardly from the lower side whereby the implantable valve is mounted to the heart when heart tissue is captured between the hooks and a surface of the lower side. The lower valved portion of the valved stent extends downwardly from the upper mounting portion. The lower valved portion includes a check valve that allows downward flow of blood and checks upward flow of blood. In an exemplary embodiment, the number N of hooks equals six.

In one implementation, the upper mounting portion extends radially and upwardly from the lower valved portion whereby the radial extent of the upper mounting portion is greater than the upward extent of the upper mounting portion. This geometry is optimal for mounting the upper mounting portion to typical heart tissue geometries above a valve such as the mitral annular tissues. The upper mounting portion has two important functions including reliably securing the valve to a location and sealing. The geometry of the upper mounting portion including the hooks is important to assure sealing between the valved stent and heart tissue to prevent leakage of blood around the periphery of the valved stent which would be equivalent to a malfunctioning valve.

The geometry of the upper mounting portion and hooks also prevents dislocation or migration of the valved stent, the latter of which is one of the most feared and adverse events associated with a replacement valve.

In another implementation, a spacing between each hook and the lower side of the upper mounting portion can be configured to accommodate variations in the geometry of heart tissue. This enables the same valved stent design to accommodate different and/or asymmetrical heart tissue geometries at the replacement site.

In a further implementation, the upper mounting portion defines a maximum radial diameter in a range of 32 to 52 millimeters. For mitral valve replacement, the maximum radial diameter can be 32 to 46 millimeters. For tricuspid valve replacement, the maximum radial diameter can be 38 to 52 millimeters. The particular radial diameter is selected based upon the geometry of the tissue above (upstream) and surrounding the valve to be replaced.

In yet another implementation, the lower valved portion of the valved stent is substantially cylindrical and defines a diameter between 28 and 30 millimeters. In one embodiment, the lower valved portion defines a diameter of about 29 millimeters.

In a further implementation, the valved stent is a family of valved stents. For each of the family, the lower valved portion is substantially cylindrical and defines a diameter between 28 and 30 millimeters. The family of valved stents has the same lower valved portion size and geometry for all family members. However, the family members have varying upper mounting portion geometries from one family member to another that defines varying maximum radial diameters. The varying maximum radial diameters can fall into a range of 32 to 52 millimeters. Mitral valve replacement family members can have upper mounting portion geometries that define maximum radial diameters with a range of 32 to 46 millimeters. Tricuspid valve replacement family members can have upper mounting portion geometries that define maximum radial diameters with a range of 38 to 52 millimeters.

In a yet further implementation, the stent is formed at least in part by cutting a metal alloy tube. The metal alloy has a shape memory type function that allows it to self-expand from the compressed state to a geometry similar to that described herein.

In a second aspect of the disclosure, a valved stent includes a stent supporting a cloth structure. The stent includes a plurality of support members that each have an upper portion and a lower vertical portion, a plurality of metal arcs that are each coupled to two of the upper portions of the support members, a plurality of hooks that are each coupled to and extend downwardly from one of the support members, and a metal mesh that is joined to the lower vertical portions of the support members to define the lower portion of the stent having a substantially cylindrical shape. The cloth structure includes a substantially cylindrical lower portion that is supported by and radially inside the metal mesh, and a check valve disposed inside the lower cylindrical portion that allows a downward flow of blood and checks upward flow of blood. In one embodiment the number of support members is N and the number of metal arcs is N. In a more particular embodiment the number of hooks is N. In a yet more particular embodiment the number N is six.

In one implementation each support member includes a bend joining the upper portion to the lower vertical portion whereby the upper portion defines an angle relative to the lower portion of more than 45 degrees. In a more particular embodiment the angle is at least 60 degrees. In a yet more particular embodiment the angle is at least 70 degrees.

In another implementation the metal arcs and the hooks mount the implantable valve by capturing annular heart tissue therebetween. A vertical spacing between the metal arcs and hooks is configurable during implantation to allow for variations in tissue thickness and geometry.

In yet another implementation each hook includes a downwardly extending proximal portion and an upwardly extending distal portion coupled by a bend.

In a further implementation the lower cylindrical portion of the cloth structure has an internal diameter between 28 and 30 millimeters. In a more particular embodiment the internal diameter is about 29 millimeters. The plurality of metal arcs define a maximum radial dimension in a range of 32 to 52 millimeters that can be varied from one valved stent to another based on a geometry of a patient's heart tissue proximate to the valve to be replaced.

In a third aspect of the disclosure, a valved stent includes a stent supporting a cloth structure. The stent includes a plurality of N support members that each have an upper portion and a lower vertical portion, a plurality of N metal arcs that are each coupled to two of the upper portions of the support members, the N metal arcs define a maximum radial dimension that is in a range of 32 to 52 millimeters, a plurality of N hooks that are each coupled to and extend downwardly from one of the support members, a vertical spacing between the metal arcs and the hooks is configurable to accommodate variations in heart tissue geometry that is captured between the metal arcs and the hooks, and a metal mesh that is joined to the lower vertical portions of the support members to define the lower portion of the stent having a substantially cylindrical shape. The cloth structure includes a substantially cylindrical lower portion that is supported by and radially inside the metal mesh and having an inside diameter of 28 to 30 millimeters, and a check valve disposed inside the lower cylindrical portion that allows a downward flow of blood and checks upward flow of blood.

An implementation of the disclosure concerns a method of implanting the valved stent that applies to any of the three aspects discussed above. The delivery of the valved stent is accomplished with a tubular device or catheter that can be inserted into a portion of the vascular system. The tubular device includes a distal end having a capsule that initially contains the valved stent in its compressed configuration for delivery. The process for implantation is as follows: (1) The distal end is routed through an arterial path to the implantation site (e.g., proximate to a diseased mitral or tricuspid valve). (2) The valved stent is translated along a central axis (central to the tubular device) relative to the distal end whereby at least part of the valved stent emerges in overlapping relation with an annular portion of the diseased valve to be replaced. The annular portion includes an opening through which the valved stent partially passes that is surrounded by annular tissue. (3) The valved stent is then allowed to radially expand to its implantation configuration. During this process the valved stent is fully released from the tubular device. Also during this process the stent is anchored to the annular tissue that is captured above and below by the upper mounting portion. It is captured above by a lower side or surface of the upper mounting portion. It is captured below by the N hooks. In one embodiment, the upper mounting portion and the N hooks are compliant and therefore bend and conform to the annular tissue to provide reliable and robust mounting and an effective seal between the lower side or surface of the upper mounting portion and an upper surface of the annular tissue.

DETAILED DESCRIPTION OF THE PREFERRED EMBODIMENTS

The embodiments of the valved stent in the summary and the devices and methods used for their proper delivery to the region of the cardiac atrioventricular or mitral valve to replace dysfunctional mitral valves and restore mitral valve function with such valved stents will be described here in further detail. There should not be any limiting to the invention or its uses by the theory or physiological principles mentioned in the background section or in the summary above or the detailed description. The following detailed description is exemplary in nature and should not be taken to be limiting to the invention, its applications or uses. Although the major application here described will be for dysfunctional mitral valves in the condition that results in mitral regurgitation, it must be kept in mind that the invention may be applied to other heart valves such as the tricuspid valve.

FIG. 1 depicts a patient's heart 2 with a valved stent 4 installed to replace a previously diseased mitral valve. Valved stent 4 has a dimensional variation that can also be utilized to replace a tricuspid valve 6.

A cylindrical coordinate system will be used in describing valved stent 4. The valved stent 4 has a central axis Z about which valved stent has a partial rotational symmetry. Rotation about central axis z is defined by an angle θ. A distance from central axis Z is defined by a radial distance R.

In defining positions terms such as upper, lower, upward, and downward will be used. Moving from lower to upper refers to an increase in the Z dimension or moving in a +Z direction. If a recited device has an upper portion and a lower portion then the upper portion is disposed in the +Z direction relative to the lower portion. The term upward or upwardly refers to the +Z direction. The term downward or downwardly refers to the −Z direction. Generally, the direction of blood flow is in the −Z or downward direction.

In defining positions, the terms "outward" or "radially outward" can be used. Moving from radially inward to radially outward refers to an increase in the R dimension or moving in a +R direction.

In one embodiment the rotational symmetry of the valved stent 4 is defined by sixty degree rotations about Z. Thus an angle θ can change by sixty degrees without any apparent physical change in valved stent 4.

Later descriptions will utilize a vertical axis Ø. Vertical axis Ø defines a rotation about R from the vertical axis Z. This is in contrast to θ which is a rotation about the central axis Z and defines the orientation of a radial line that intersects the central axis Z.

Figure 2A:
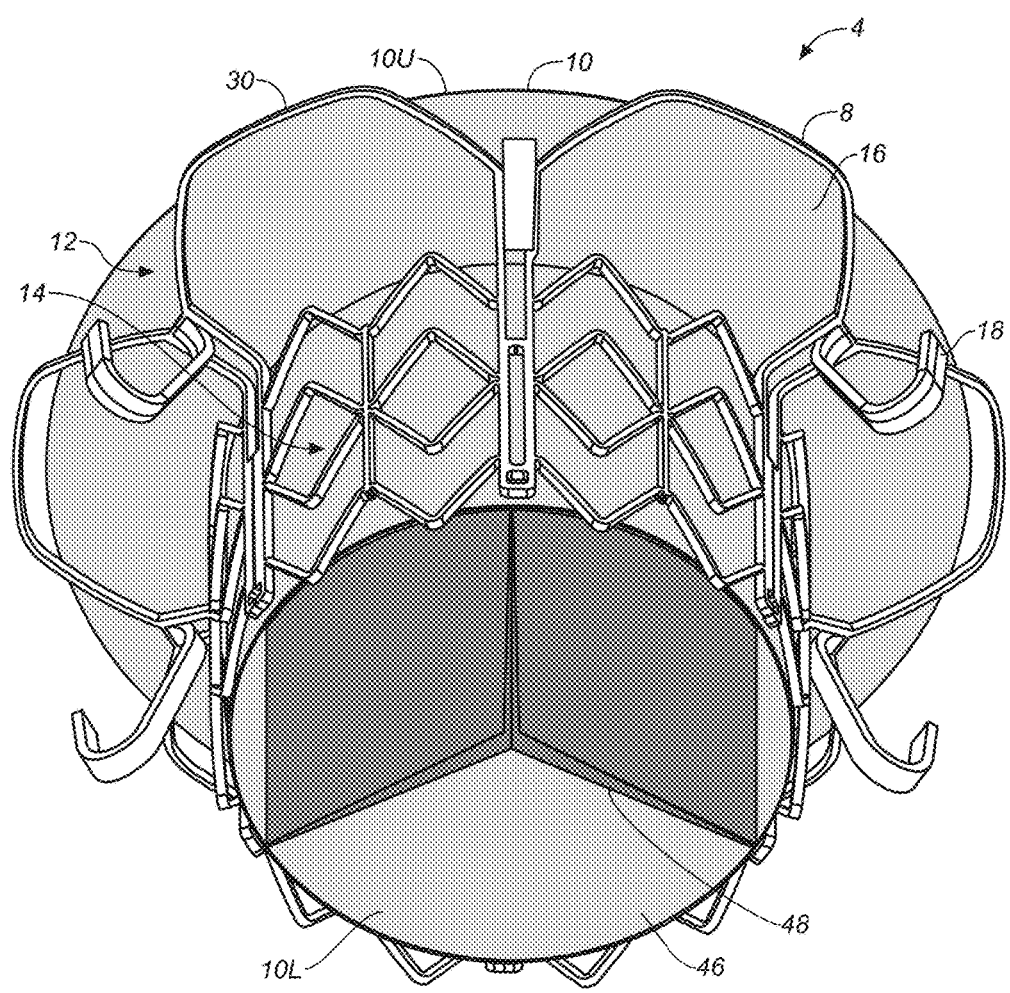
FIG. 2A is a lower side isometric view of a valved stent.
Figure 2B:
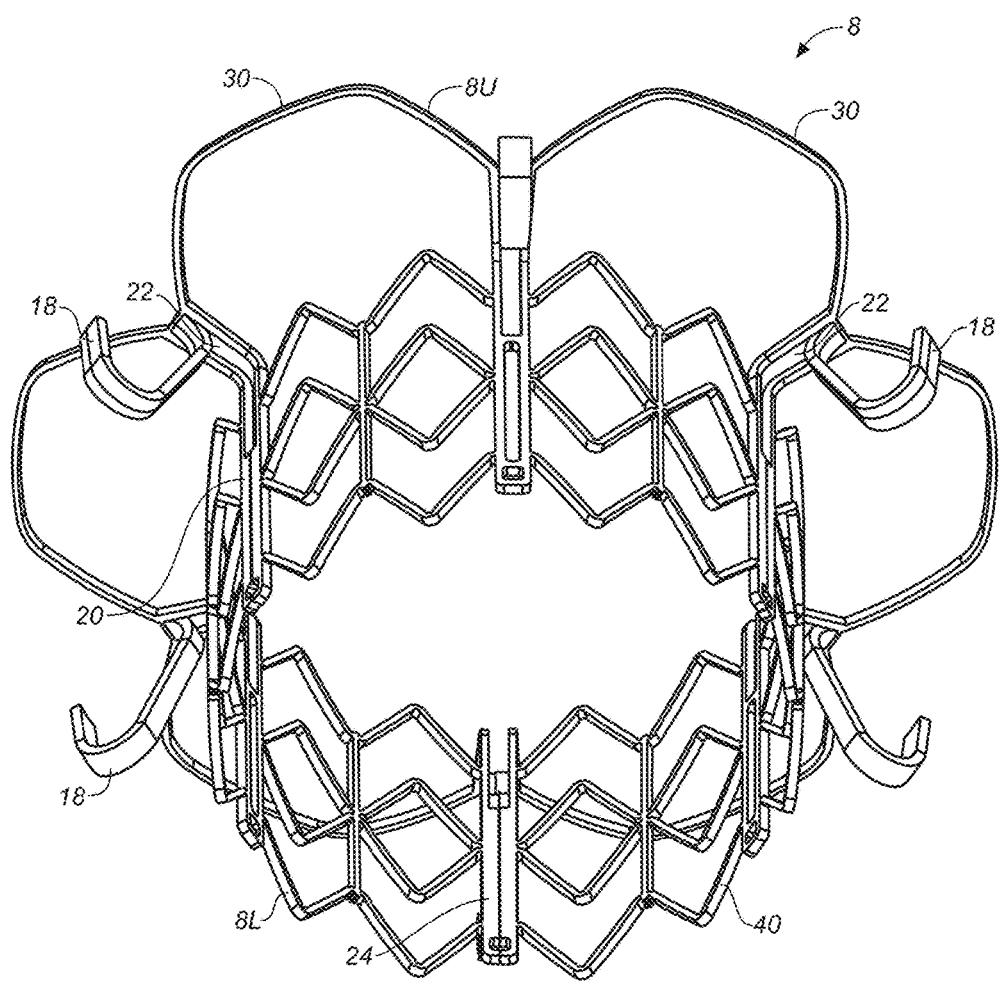
FIG. 2B is a lower side isometric view of a stent that forms part of a valved stent.
Figure 3:
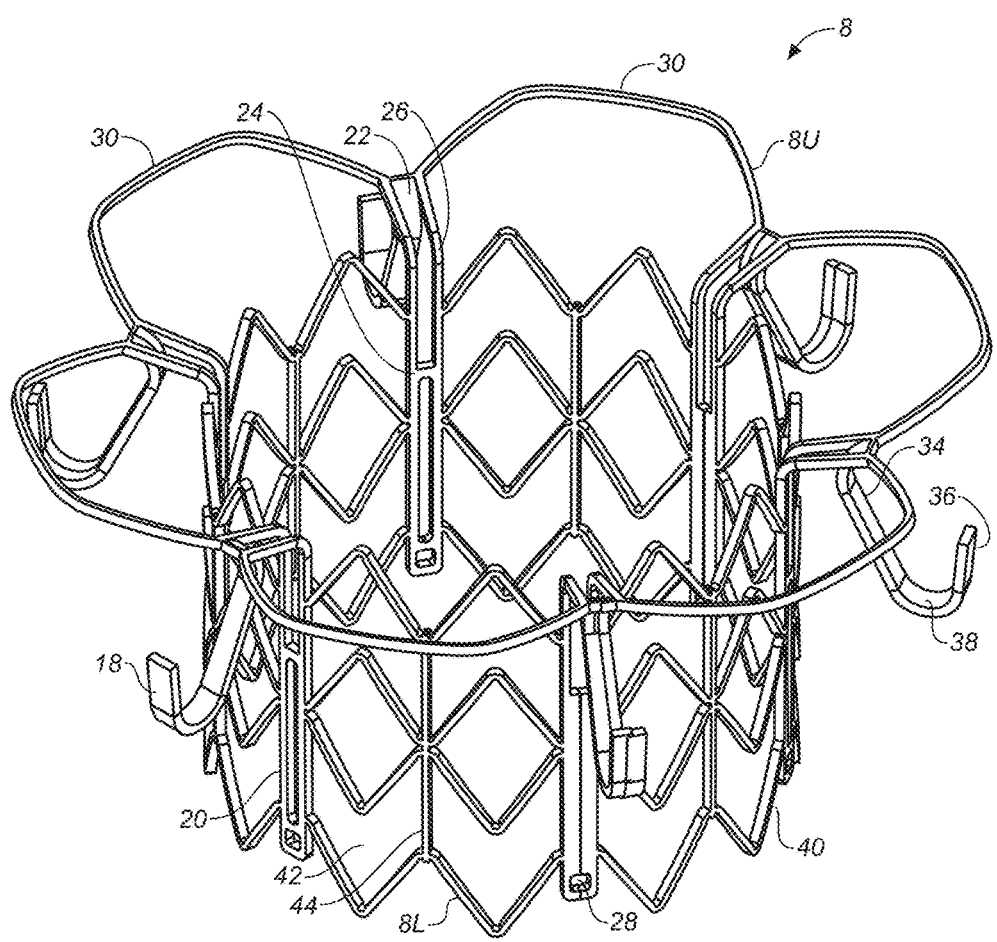
FIG. 3 is an upper side isometric view of a stent that forms part of a valved stent.

FIGS. 2A, 2B, and 3 depict additional details of valved stent 4 in an expanded or partially expanded state after delivery to a site to be implanted. Referring to FIG. 2A, valved stent 4 includes a stent 8 supporting a cloth structure 10. FIGS. 2B and 3 depict the stent 8 without the cloth structure 10 disposed at two different orientations of the central axis Z relative to the figure perspective.

The valved stent 4 has two major portions including an upper mounting portion 12 and a lower valved portion 14. The upper mounting portion 12 extends radially (+R) and upwardly (+Z) from the lower valved portion 14. The radial extent of the upper mounting portion is greater than the upward extent. In one embodiment, the radial extent is at least 1.5 times the upward extent. In another embodiment, the radial extent is at least twice the upward extent. In a particular embodiment the upper mounting portion has a substantially conical shape with a surface slope that is more than 45 degrees from vertical as measured by Ø. In a more particular embodiment, the surface slope is more than 60 degrees from the vertical as measured by Ø. Thus, the upper mounting portion 12 is primarily radially or laterally extending from the lower valved portion 14.

The upper mounting portion 12 is for mounting the valved stent 4 to heart tissue in replacing the function of a mitral or tricuspid valve. The upper mounting portion 12 has a lower side 16 that faces downwardly and slightly outwardly. Extending downwardly from the lower side 16 are a plurality of hooks 18. The valved stent 4 is secured to heart 2 when a layer of heart tissue is captured between lower side 16 and hooks 18.

The lower valved portion 14 extends downwardly from the upper mounting portion 12. The lower valved portion 14 is substantially cylindrical in shape whereby it extends downwardly in a direction corresponding to a value of ∅ equal to zero or nearly so.

Each of the stent 8 and the cloth structure 10 have upper and lower portions corresponding to the upper mounting portion 12 and lower valved portion 14. The stent 8 upper and lower portions will be referred to as 8U and 8L respectively. The cloth structure 10 upper and lower portions will be referred to as 10U and 10L respectively.

Coupling the upper 8U and lower 8L portions of stent 8 are a plurality of support members 20. In an exemplary embodiment there are six support members 20. Each support member 20 includes an upper portion 22 and a lower portion 24 that are joined by a bend 26. The bend defines an angle of more than 45 degrees. In one embodiment the bend defines an angle in the range of 50 to 90 degrees. In another embodiment the bend defines an angle in the range of 60 to 80 degrees. In a particular embodiment the bend defines about a 70 degree angle whereby the upper portion extends in a direction that is about 70 degrees from the vertical and generally radially outward. At least some of the support members 20 define openings 28 near their lower end which are for attachment and delivery of the valved stent 4.

Coupled to the upper portion 22 of each support member 20 are two metal arcs 30. Each metal arc 30 defines a petal shape. Each metal arc 30 is also joined to two support members 20. Thus the number N of metal arcs 30 equals the number N of support members 20. In the illustrative embodiment the number N of metal arcs 30 is six.

Coupled to a lower side of each upper portion 22 of each support member 20 is a hook 18. Each hook 18 extends downwardly from the upper portion 22 of the support member 20. Each hook 18 has a proximal portion 34 that extends downwardly, a distal portion 36 that extends upwardly, and a bend 38 that joins the proximal portion 34 and the distal portion 36 (FIG. 3).

When the valved stent 4 is mounted in a patient's heart 2, a layer of heart tissue is captured between the metal arcs 30 and the hooks 18. Before the valved stent 4 is mounted in a patient's heart 2, the upper mounting portion 12 of the valved stent 4 is symmetrical. However, the geometry of heart tissue proximate to a site for valved stent 4 can vary dramatically from one heart to another. The tissue geometry may be very asymmetrical and vary in thickness. During deployment of the valved stent 4, a spacing along the Z axis between the metal arcs 30 and the hooks 18 can be conformed to the geometry of the heart tissue. After placement of the valved stent 4, the geometry of the upper mounting portion 12 may be asymmetric because the vertical distance along the Z axis between metal arcs 30 and hooks 18 will vary in Z.

The upper portion 10U of the cloth structure 10 is disposed above the metal arcs 30. The upper portion 10U of the cloth structure 10 is also attached to the metal arcs 30.

Coupled to the lower portion 24 of each support member 20 is a metal mesh 40. The combination of the lower portions 24 of the support members 20 and the metal mesh 40 define the lower portion 8L of the stent 8. In the illustrative embodiment the wires of the metal mesh 40 have a zigzag geometry that defines diamond-shaped and chevron-shaped openings 42. Joining the zigzag wires of metal mesh 40 are vertical cross members 44. The lower portion 8L of stent 8 has a substantially cylindrical geometry that substantially defines or defines a right cylinder.

Figure 4:
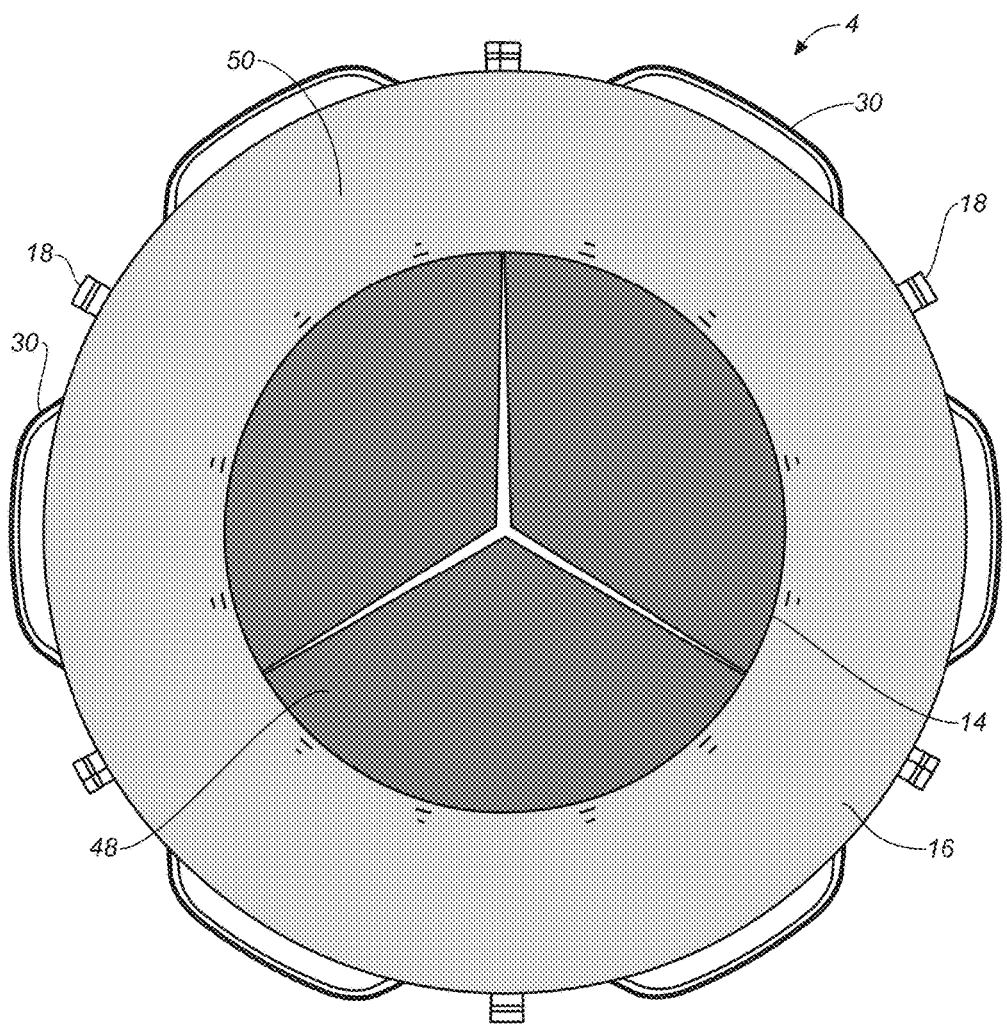
FIG. 4 is a top view of a valved stent.

The lower portion 10L of cloth structure 10 includes a cylindrical portion 46 that is disposed inside the lower portion 8L of stent 8. Cylindrical portion 46 is disposed radially inward (−R) relative to the lower portion 8L. Inside cylindrical portion 46 of cloth structure 10 is a check valve 48 (FIG. 4). Check valve 48 allows a downward (−Z) flow of blood through valved stent 4. Check valve checks (stops or impedes) an upward (+Z) flow of blood through valved stent 4.

FIG. 4 depicts a top view of valved stent 4. From this view, check valve 48 and a top side 50 of the upper mounting portion 12 are visible. From this view the stent 8 is mostly covered by the cloth structure 10. However, the radially extending tips of hooks 18 and metal arcs 30 can be seen in the illustrative embodiment.

Figure 5:
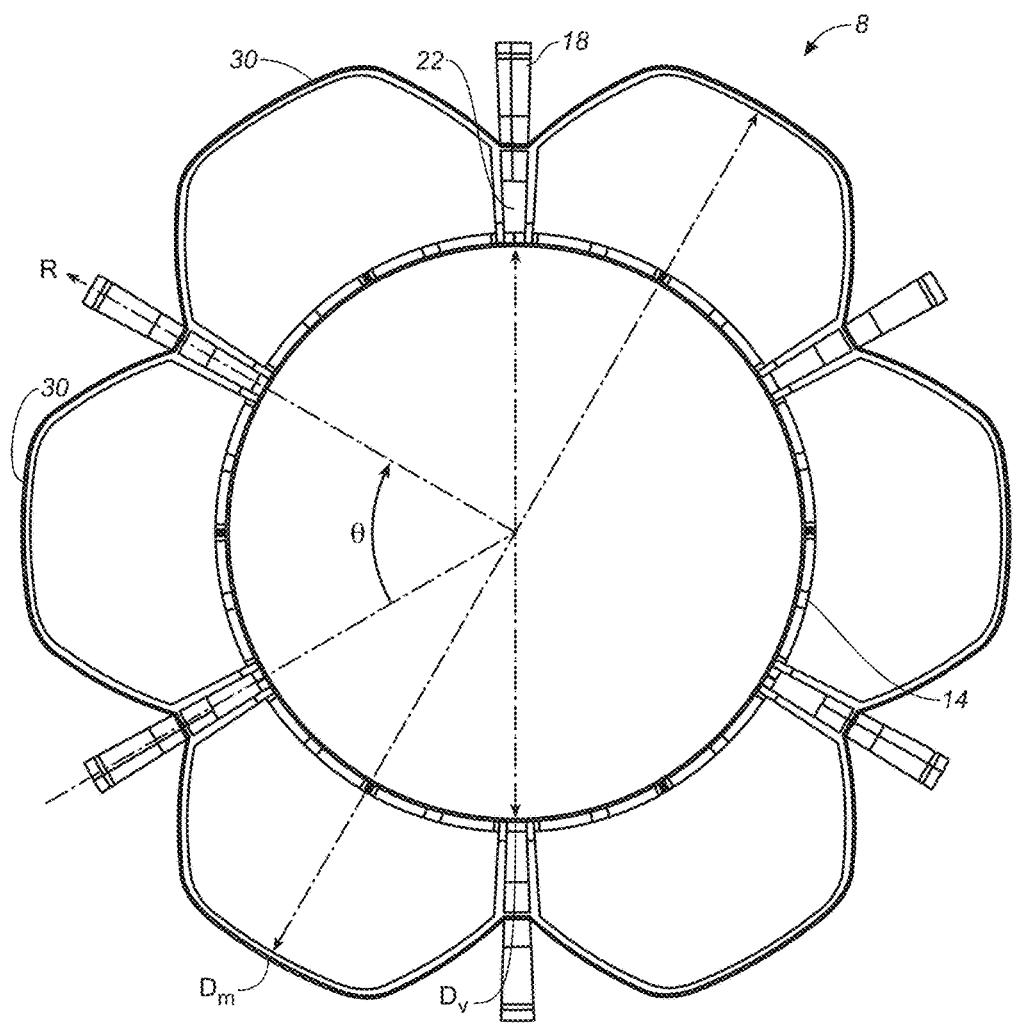
FIG. 5 is a top view of a stent that forms part of a valved stent.

FIG. 5 depicts a top view of stent 8. The radial axis R and angle θ are illustrated. The upper portions 22 of the six support members 20 are positioned at angular positions for which the angle θ equals 0, 60, 120, 180, 240, and 300 degrees and thus separated by 60 degrees. Extending downwardly from each upper portion 22 is a hook 18. Thus, the six hooks 18 have the same six angular positions as the six support members 20. Between closest upper portions 22 of support members 20 are metal arcs 30. One metal arc extends radially and angularly throughout an angular θ range of zero to sixty degrees. The next metal arc extends radially and angularly throughout an angular θ range of 60 and 120 degrees, and so on. Thus each metal arc extends radially outward and inward while subtending an angle of nearly 60 degrees.

Opposing pairs of metal arcs 30 define a maximum radial dimension $D_m$ of the upper mounting portion. Opposing pairs of metal arcs 30 are defined by those intersected with a diametrical line that passes through the central axis Z. $D_m$ has a potential range of 32 to 52 millimeters that is dependent upon the heart geometry where the valve replacement is to take place. A range of 32-46 millimeters is for the mitral valve and a range of 38-52 millimeters is for the tricuspid valve. In one embodiment for a mitral valve the radial span of the pedals is about 37 millimeters. For a given valve (mitral or tricuspid) the value of $D_m$ is dependent upon the particular geometry of a patient's heart.

The lower valved portion 14 has a diameter $D_v$ of 28 to 30 millimeters. In an exemplary embodiment, the lower valved portion 14 has a diameter $D_v$ of about 29 mm. A further embodiment includes a family of valved stents 4 each having a set lower valved portion 14 diameter $D_v$ equal to about 29 millimeters. This family will have a variety of upper mounting portion 12 diameters $D_m$ to accommodate different patients and different valve replacements.

Figure 6:
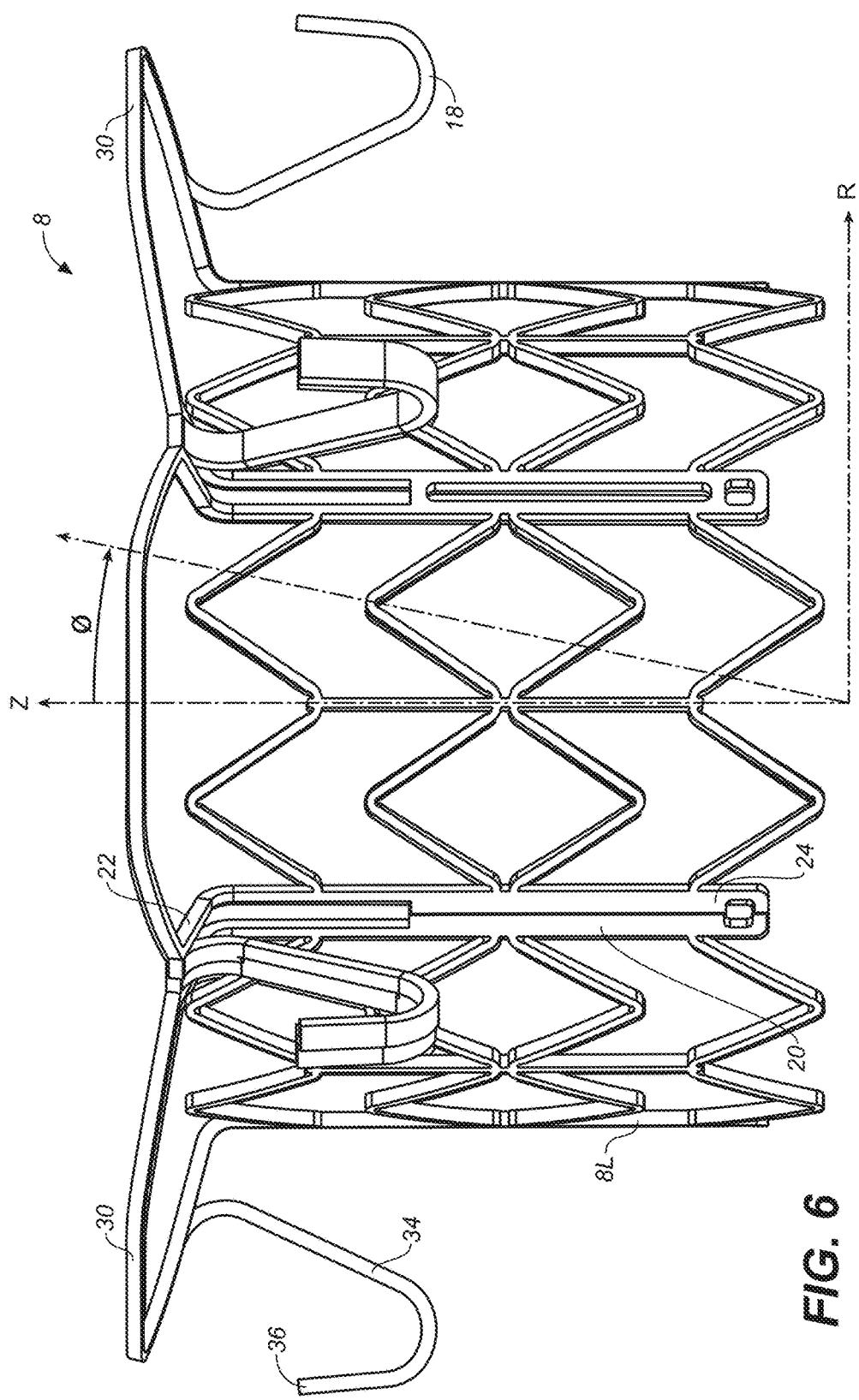
FIG. 6 is a side view of a stent that forms part of a valved stent.

FIG. 6 depicts a side view of stent 8. An axis Ø defines an angle from vertical axis Z. The metal arcs 30 extend radially and upwardly in the illustrated embodiment but most of the extension is radial. The extension of each metal arc 30 defines an angle Ø that is more than 45 degrees, more than 60 degrees, or in a range of 60 to 90 degrees. The larger angle Ø allows the lower side of upper mounting portion 12 to be close to the geometry of heart tissue on the entrance side of a valve.

Each hook 18 extends radially outward. The proximal portion 34 of each hook 18 extends downwardly and radially outward with an angle Ø that is in a range of about 20 to 30 degrees or about 25 degrees. The distal end 36 of each hook 18 extends upwardly and radially outwardly but nearly vertical. The distal end 36 of each hook is about six millimeters below the metal arc 30 in Z. As a note these angles and dimensions are exemplary and can be optimized for a particular heart geometry. The lower portion 8L of stent 8 defines a shape that is very nearly a right circular cylinder whose curved side is nearly coincident with an angle Ø of zero.

The disclosed valved stent 4 is delivered to an implantation site in a radially compressed form. Upon proper positioning as in FIG. 1, the valved stent 4 is expanded or allowed to expand. Upon expansion, the valved stent 4 has a geometry similar to that illustrated with respect to the previously described figures.

The specific embodiments and applications thereof described above are for illustrative purposes only and do not preclude modifications and variations encompassed by the scope of the following claims.

What we claim is:

1. A valved stent for a patient heart comprising:
   a stent supporting a cloth structure together forming the valved stent, the valved stent further comprising:
   an upper mounting portion having an upper side and a downward facing lower side and including a plurality of hooks each having a proximal portion extending downwardly from the lower side and a distal portion that extends upwardly, the upper mounting portion including a plurality of metal arcs that support an upper portion of the cloth structure and each extend outwardly between pairs of the hooks whereby the implantable valve is mounted to the heart when heart tissue is captured between the hooks and the metal arcs; and
   a lower valved portion extending downwardly from the upper mounting portion, the lower valved portion including a check valve that allows downward flow of blood and checks upward flow of blood.

2. The implantable valved stent of claim 1 wherein the upper mounting portion extends radially and upwardly from the lower valved portion, the radial extent is greater than the upward extent.

3. The implantable valved stent of claim 1 wherein a spacing between each hook and the lower side can be configured during implantation to accommodate variations in the geometry of the heart tissue.

4. The implantable valved stent of claim 1 wherein the cloth structure of the upper mounting portion is attached above the stent of the upper mounting portion.

5. The implantable valved stent of claim 1 wherein the plurality of hooks includes six hooks.

6. The implantable valved stent of claim 1 wherein the upper mounting portion defines a maximum diameter in a range of 32 to 52 millimeters.

7. The implantable valved stent of claim 1 wherein the upper mounting portion defines a maximum diameter in a range of 32 to 46 millimeters for a mitral valve replacement.

8. The implantable valved stent of claim 1 wherein the upper mounting portion defines a maximum diameter in a range of 38 to 52 millimeters for a tricuspid valve application.

9. The implantable valved stent of claim 1 wherein the lower valved portion is substantially cylindrical and defines a diameter between 28 and 30 millimeters.

10. An implantable valved stent comprising:
    a stent having an upper portion and a lower portion and including:
    a plurality of support members that each have an upper portion and a lower vertical portion;
    a plurality of metal arcs that are each coupled to two of the upper portions of the support members;
    a plurality of hooks that are each coupled to and extend downwardly from one of the support members; and
    a metal mesh that is joined to the lower vertical portions of the support members to define the lower portion of the stent having a substantially cylindrical shape; and
    a cloth structure supported by the stent and including:
    an upper portion that is disposed above and supported by the metal arcs; and
    a substantially cylindrical lower portion that is supported by and radially inside the metal mesh; and
    a check valve disposed inside the lower cylindrical portion that allows a downward flow of blood and checks an upward flow of blood.

11. The implantable valved stent of claim 10 wherein for each support member a bend joins the upper portion to the lower vertical portion whereby the upper portion defines an angle relative to the lower portion of more than 45 degrees.

12. The implantable valved stent of claim 10 wherein the number of support members is N and the number of metal arcs is N.

13. The implantable valved stent of claim 12 wherein number of hooks is N.

14. The implantable valved stent of claim 13 wherein N is six.

15. The implantable valved stent of claim 10 wherein the metal arcs and the hooks mount the implantable valve by capturing heart tissue therebetween, a vertical spacing between the metal arcs and hooks is configurable during implantation to allow for variations in tissue thickness and geometry.

16. The implantable valved stent of claim 10 wherein each hook includes a downwardly extending proximal portion and an upwardly extending distal portion coupled by a bend.

17. The implantable valved stent of claim 10 wherein the lower cylindrical portion of the cloth structure has an internal diameter between 28 and 30 millimeters.

18. The implantable valved stent of claim 17 wherein the plurality of metal arcs define a maximum radial dimension in a range of 32 to 52 millimeters that can be varied from one valved stent to another based on a geometry of a patient's heart tissue proximate to the valve to be replaced.

19. An implantable valved stent comprising:
    a stent having an upper portion and a lower portion and including:
    a plurality of N support members that each have an upper portion and a lower vertical portion separated by a bend in the support member;
    a plurality of N metal arcs that are each coupled to two of the upper portions of the support members, the N metal arcs define a maximum radial dimension that is in a range of 32 to 52 millimeters;
    a plurality of N hooks that are each coupled to and extend downwardly from one of the support members, a vertical spacing between the metal arcs and the hooks is configurable to accommodate variations in heart tissue geometry that is captured between the metal arcs and the hooks;
a metal mesh that is joined to the lower vertical portions of the support members to define the lower portion of the stent having a substantially cylindrical shape; and
a cloth structure supported by the stent and including:
an upper portion that is disposed above and supported by the metal arcs;
a substantially cylindrical lower portion that is supported by and radially inside the metal mesh and having an inside diameter of about 28 to 30 millimeters; and
a check valve disposed inside the lower cylindrical portion that allows a downward flow of blood and checks an upward flow of blood.

* * * * *